United States Patent
Karlstedt

(10) Patent No.: US 9,724,059 B2
(45) Date of Patent: Aug. 8, 2017

(54) SYSTEMS AND METHODS FOR COOLING X-RAY TUBES AND DETECTORS

(71) Applicant: Laird Technologies, Inc., Earth City, MO (US)

(72) Inventor: Dan Martin Gustav Karlstedt, Torslanda (SE)

(73) Assignee: Laird Technologies, Inc., Earth City, MO (US)

(*) Notice: Subject to any disclaimer, the term of this patent is extended or adjusted under 35 U.S.C. 154(b) by 275 days.

(21) Appl. No.: 14/666,401

(22) Filed: Mar. 24, 2015

(65) Prior Publication Data

US 2015/0194286 A1    Jul. 9, 2015

Related U.S. Application Data

(63) Continuation of application No. PCT/US2013/051195, filed on Jul. 19, 2013.
(Continued)

(51) Int. Cl.
*H05G 1/02* (2006.01)
*H01J 7/26* (2006.01)
(Continued)

(52) U.S. Cl.
CPC .............. *A61B 6/4488* (2013.01); *H01J 7/26* (2013.01); *H01L 23/46* (2013.01); *H01L 23/473* (2013.01);
(Continued)

(58) Field of Classification Search
CPC .... A61B 6/00; A61B 6/02; A61B 6/03; A61B 6/035; A61B 6/44; A61B 6/4488;
(Continued)

(56) References Cited

U.S. PATENT DOCUMENTS

| 7,104,687 | B2 * | 9/2006 | Okamura | A61B 6/40 |
| | | | | 250/370.15 |
| 7,186,021 | B1 * | 3/2007 | Breham | H01J 35/16 |
| | | | | 378/199 |

(Continued)

FOREIGN PATENT DOCUMENTS

| DE | 10331522 A1 | 2/2005 |
| EP | 2343586 A1 | 7/2011 |

(Continued)

OTHER PUBLICATIONS

European Office Action dated Mar. 29, 2016 for EP application No. 13845126.5 filed Apr. 1, 2015 which claims priority to the same parent application as the instant application; 7 pages.

(Continued)

*Primary Examiner* — Anastasia Midkiff
(74) *Attorney, Agent, or Firm* — Harness, Dickey & Pierce, P.L.C.

(57) ABSTRACT

According to various aspects, exemplary embodiments are disclosed of systems that may be used for cooling objects, such as X-ray tubes and detectors, etc. Also disclosed are exemplary embodiments of methods for cooling objects, such as X-ray tubes and detectors, etc. For example, an exemplary embodiment includes a system that can be used to cool an X-ray tube and detector with one chiller. As another example, an exemplary embodiment of a method includes using one chiller to cool an X-ray tube and detector.

21 Claims, 6 Drawing Sheets

Related U.S. Application Data

(60) Provisional application No. 61/712,802, filed on Oct. 11, 2012, provisional application No. 61/713,349, filed on Oct. 12, 2012, provisional application No. 61/714,295, filed on Oct. 16, 2012.

(51) Int. Cl.

| | | |
|---|---|---|
| *H01L 23/34* | (2006.01) | |
| *H01L 23/46* | (2006.01) | |
| *A61B 6/00* | (2006.01) | |
| *H01L 23/473* | (2006.01) | |

(52) U.S. Cl.
CPC ....... *H05G 1/025* (2013.01); *F04C 2270/041* (2013.01); *H01L 23/34* (2013.01)

(58) Field of Classification Search
CPC . H05G 1/00; H05G 1/02; H05G 1/025; H01L 27/00; H01L 27/146; H01L 27/14618; H01L 27/14658; H01L 27/14676; H01L 27/148; H01L 27/14806; H01L 27/16; H01L 23/00; H01L 23/34; H01L 23/36; H01L 23/367; H01L 23/373; H01L 23/3738; H01L 23/38; H01L 23/46; H01L 23/473; H01L 35/00; H01L 35/02; H01L 35/04; H01L 35/28; H01L 35/30; H01L 35/32; H01L 35/34; H01L 37/00; H01J 7/24; H01J 7/26; H01J 19/74; H01J 35/00; H01J 35/02; F24F 5/00; F24F 5/0003; F24F 5/0042; F25B 29/00; F25B 29/003; F25B 30/00; F25B 21/00; F25B 21/02; F25B 21/04; F25B 2321/00; F25B 2321/02; F25B 2321/021; F25B 2321/023; F25B 2321/025; F25B 2321/0252; F25B 2600/25; F25B 2600/2507; F25B 2600/2515
See application file for complete search history.

(56) References Cited

U.S. PATENT DOCUMENTS

| | | |
|---|---|---|
| 2004/0234040 A1 | 11/2004 | Okamura et al. |
| 2009/0261238 A1 | 10/2009 | Ahn et al. |
| 2011/0291017 A1 | 12/2011 | Frach |
| 2012/0106709 A1 | 5/2012 | Hockersmith et al. |

FOREIGN PATENT DOCUMENTS

| | | |
|---|---|---|
| JP | 2005-317316 | 11/2005 |
| JP | 2007-123211 | 5/2007 |
| JP | 2009059743 | 3/2009 |
| KR | 20-0142766 | 6/1999 |
| WO | WO 2014/058501 | 4/2014 |

OTHER PUBLICATIONS

Chinese Office Action dated Apr. 5, 2016 for Chinese application No. 201380053111.2 filed Apr. 10, 2015 which claims priority to the same parent application as the instant application; 11 pages.

International Search Report and Written Opinion dated Nov. 11, 2013 for PCT App. No. PCT/US2013/051195 (published as WO 2014/058501) which is the parent application to the instant application; 13 pages.

Dell H2C Technology: Hybrid Cooling For Overclocked CPUs, White Paper Jan. 2007, DELL™, www.dell.com/h2c, Copyright 2007; 5 pages.

MTEC by CoolIT Systems, Corporate Presentation; Feb. 2007; 30 pages.

Manual WLK 50 SP, YXLON International, Dec. 2005, 17 pages.

CoolIT Systems™ the new standard for cooling computers, www.coolitsystems.com, accessed Oct. 12, 2012, 39 pages.

M. Davis et al., Thermoelectric CPU Cooling using High Efficiency Liquid Flow Heat Exchangers; Hydrocool Pty Ltd., printed Oct. 12, 2012, 4 pages.

Liquid Cooling Systems Solutions; www.lairdtech.com; THR-BRO-LCS 1111, Copyright 2011, 6 pages.

Online Catalog; Liquid Cooling Systems on Laird Technologies, http://lairdtech.thomasnet.com/viewitems/thermal-management-solutions/wl-series-liquid; Copyright 2011, 2 pages.

Thermoelectric Assemblies / TEAs, http://www.lairdtech.com/Procuts/Thermal-Management-Solutions/Thermoelectric-Asse . . . , Copyright 2012, 5 pages.

Online Catalog; Direct Liquid Systems (DL) Assemblies on Laird Technologies, Copyright 2011, http://lairdtech.thomasnet.com/viewitems/thermal-electric-assemblies/direct-liquid-systems . . . , 1 pages.

Thermoelectric Module / TEM; http://www.lairdtech.com/Products/Thermal-Management-Solutions/Thermoelectric-Mod . . . Copyright 2012; 6 pages.

Liquid Cooling Systems Systems, http://www.lairdtech.com/Products/Thermal-Management-Solutions/Liquid-Cooling-syst..,. Copyright 2012; 3 pages.

European Partial Supplementary Search Report issued in European Patent Application No. 13845126.5, dated Sep. 4, 2015, which claims the same priority as the instant application; 7 pgs.

* cited by examiner

SYSTEMS AND METHODS FOR COOLING X-RAY TUBES AND DETECTORS

CROSS-REFERENCE TO RELATED APPLICATIONS

This patent application is a continuation of and claims the benefit of International Application No. PCT/US2013/051195 filed Jul. 19, 2013 (published as WO 2014/058501 on Apr. 17, 2014) which, in turn, claims the benefit of and priority to U.S. Provisional Patent Application No. 61/712,802 filed Oct. 11, 2012, U.S. Provisional Patent Application No. 61/713,349 filed Oct. 12, 2012, and U.S. Provisional Patent Application No. 61/714,295 filed Oct. 16, 2012. The entire disclosures of each of the above applications are incorporated herein by reference.

FIELD

The present disclosure relates to systems and methods that may be used for cooling X-ray tubes and detectors.

BACKGROUND

This section provides background information related to the present disclosure which is not necessarily prior art.

FIG. 1 generally illustrates the basics of using two different chillers 1 and 3 for cooling an X-ray tube 29 and an X-ray image detector 31. Specifically, the first chiller 1 is used for cooling the X-ray tube 29, while the second chiller 3 is used for cooling the X-ray image detector 31.

The first chiller 1 in the X-ray tube loop may be an active chiller. In which case, the active chiller has a built-in air conditioning (AC) loop that, along with a liquid to liquid heat exchanger, cools the secondary fluid comprised of water mixed with a corrosion inhibitant. The AC loop includes a compressor, a condenser, a fan, and an evaporator. The secondary loop with water consists of a heat exchanger, a pump 5, and an accumulator. With this set up, high cooling capacity below ambient temperature can be achieved.

If the first chiller 1 is passive, the X-ray loop just consists of a radiator (air to liquid heat exchanger), a fan, and a pump. With a passive chiller, however, temperatures below ambient cannot be obtained.

The X-ray image detector has to be kept at a certain stable temperature to obtain good quality of the images. There are different possible ways to cool X-ray image detectors, such as using cold plates.

FIG. 1 shows the complete system assembled together with long flexible hoses 9, 11, 13, and 15. The flexible hoses 9, 11, 13, and 15 are relatively long because the chillers 1 and 3 are situated far from the actual X-ray machine. This is due to the fact that there can be no parts in the operating area stirring the air or making noise. The chillers 1 and 3 are situated in a technical room often tens of meters away and on an opposite side of a wall 17 than the X-ray tube 29 and X-ray image detector 31.

Also shown in FIG. 1 are arrows 19, 21, 23, and 25 representing the coolant flow or circulation (e.g., via pumps 5 and 7, etc.) through the system. More specifically, the arrow 19 represents the coolant flow from the first chiller 1 through the hose 9 to the X-ray tube 29. The arrow 21 represents the coolant flow from the X-ray tube 29 through the hose 11 back to the first chiller 1. The arrow 23 represents the coolant flow from the second chiller 3 through the hose 13 to the X-ray detector 31. The arrow 25 represents the coolant flow from the X-ray detector 31 through the hose 15 back to the second chiller 3.

FIG. 2 shows an example of a cold plate 27 of a X-ray image detector. In operation, the cold plate 27 works as a heat spreader. The cold plate 27 may be made of aluminium in order to provide a good heat spread. The actual detector itself (not shown) is placed on or mounted to the cold plate 27.

SUMMARY

This section provides a general summary of the disclosure, and is not a comprehensive disclosure of its full scope or all of its features.

According to various aspects, exemplary embodiments are disclosed of systems that may be used for cooling objects, such as X-ray tubes and detectors, etc. Also disclosed are exemplary embodiments of methods for cooling objects, such as X-ray tubes and detectors, etc. For example, an exemplary embodiment includes a system that can be used to cool an X-ray tube and detector with one chiller. As another example, an exemplary embodiment of a method includes using one chiller to cool an X-ray tube and detector.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

The inventor hereof has recognized that combining a chiller (passive or active) and an active DL (direct to liquid or direct liquid) peltier cooler to provide cooling only where it is needed (e.g., "spot cooling") can reduce the energy needed to cool an X-ray detector. In exemplary embodiments disclosed herein, there is passive chiller/active "spot" cooling that allows for reductions in energy needed for cooling an X-ray detector while also allowing for removal and elimination of insulation for fluid conduits (e.g., tubes, hoses, tubing, pipes, etc.) through which the coolant flows that connects the passive and active parts as described below. The reduced power consumption and elimination of the need for insulated fluid conduits allows for reduced costs.

In an exemplary embodiment, a system is configured to cool a detector plate of an X-ray system. This exemplary embodiment includes a passive or active cooler, such as an active chiller with 6000 watts (W) of cooling power, etc. The chiller is on the outside of the operating environment for the X-ray detector. There is at least one direct-liquid (DL) thermoelectric assembly (TEA) at (e.g., situated on, mounted, to, etc.) the X-ray detector plate to be cooled, which thus provides spot cooling of the X-ray detector plate. In operation, coolant travels from the chiller through one or more fluid conduits to the at least one DL TEA (direct-liquid thermoelectric assembly), which is used to actively cool the X-ray detector plate.

Figure 1:
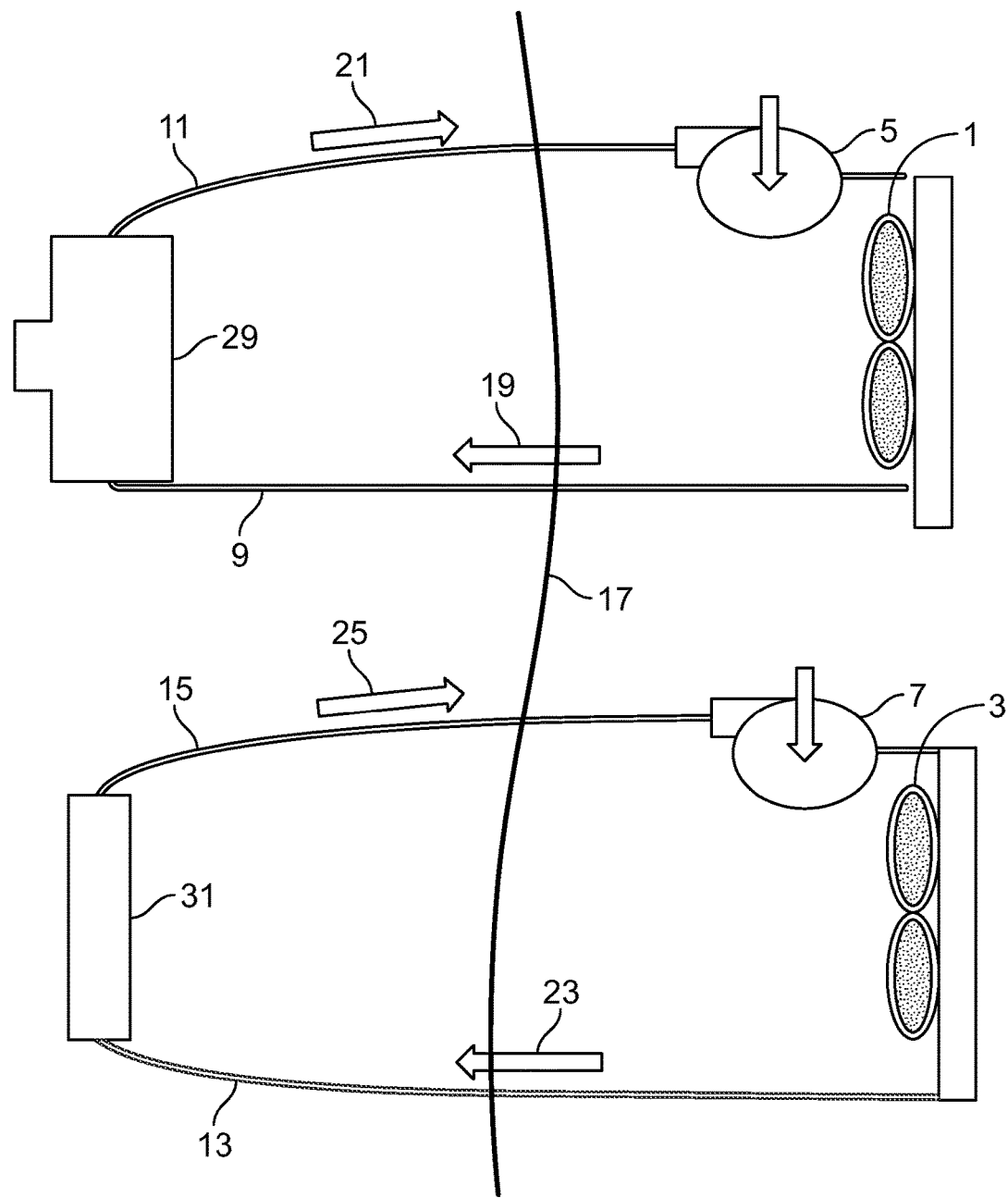
FIG. 1 illustrates a conventional way that two different chillers may be used to respectively cool an X-ray tube and an X-ray detector.
Figure 2:
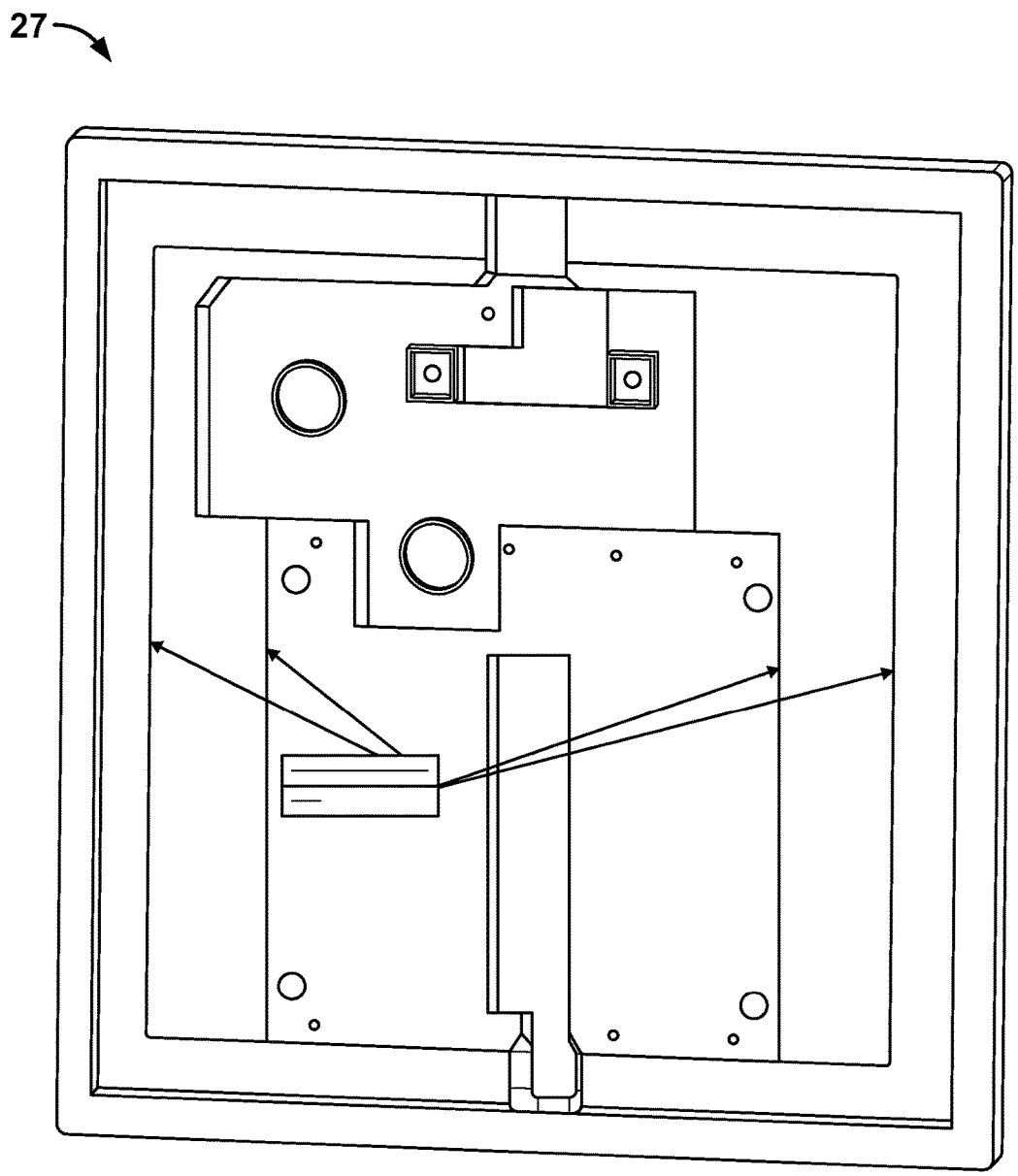
FIG. 2 illustrates an example of a cold plate of a X-ray image detector.
Figure 3:
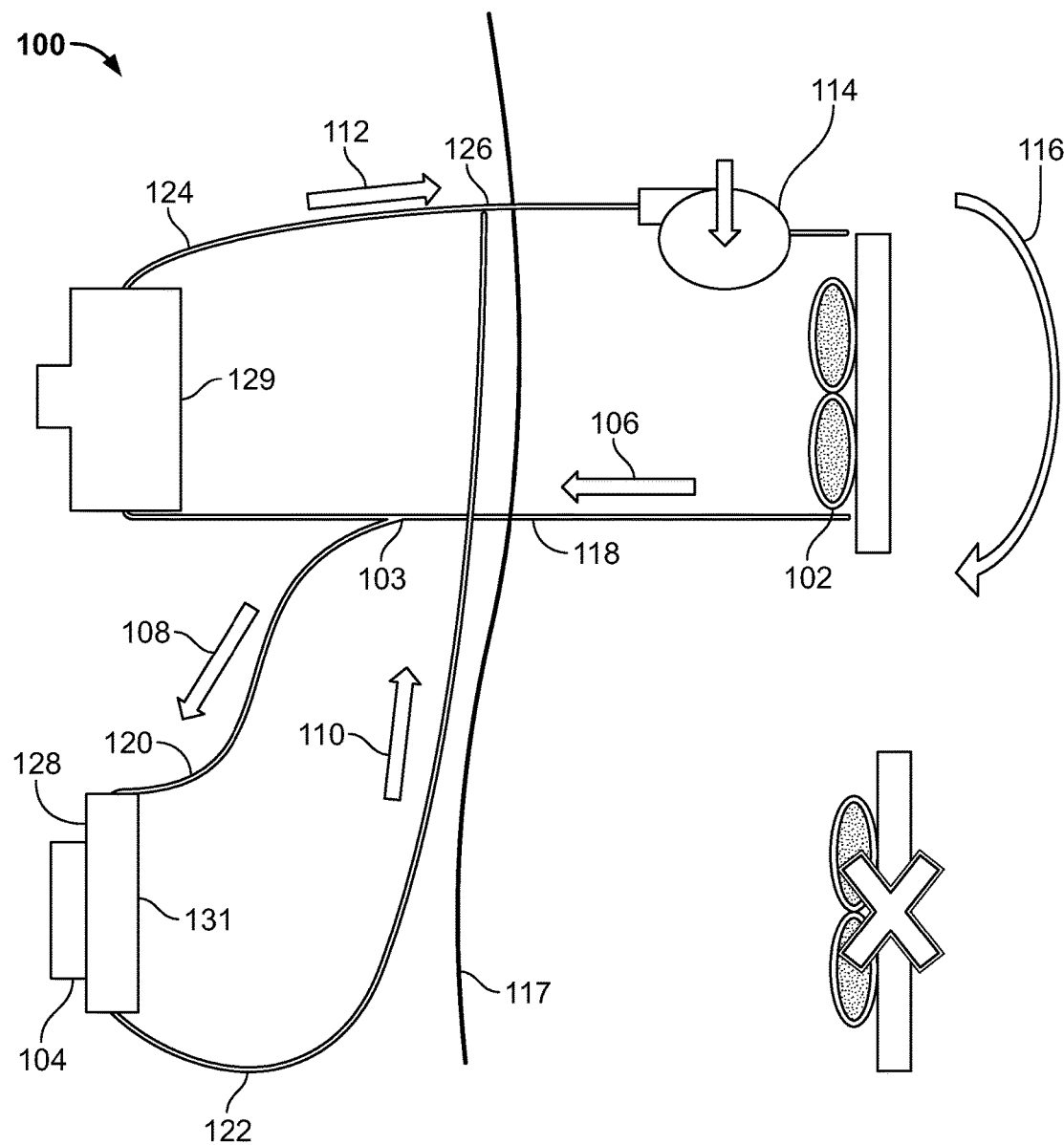
FIG. 3 illustrates an exemplary embodiment of a system for cooling an X-ray tube and an X-ray detector plate with a single chiller.

With reference now to the figures, FIG. 3 illustrates an exemplary embodiment of a system 100 embodying one or more aspects of the present disclosure. As shown in FIG. 3, the system 100 may be used for cooling an X-tray tube 129 and an X-ray image detector 131 with a single chiller 102. Accordingly, the same chiller 102 from the X-ray tube 129 is also used for cooling the X-ray image detector 131. The chiller 102 may be situated in a technical room on an opposite side of a wall 117 than the X-ray tube 129 and X-ray image detector 131.

The chiller 102 may be an active or passive chiller depending on the cooling needs of the X-ray tube 129. By way of example only, the chiller 102 may be a WLK60 recirculating chiller from Laird Technologies, Inc. having a cooling capacity of 6000 watts. By using such a heavy duty chiller with a cooling capacity of 6000 watts for the X-ray tube 129, some of the cooling capacity (e.g., about 20 to 300 watts, etc.) can be spared and used for cooling the detector 131.

A portion of the coolant from the chiller 102 is diverted to at least one active DL (direct to liquid or direct liquid) thermoelectric assembly (TEA) 104. For example, the portion of the coolant from the chiller 102 may be diverted by a valve, an installation configured to branch the coolant flow, etc. at location or juncture 103.

The DL TEA 104 is situated on or mounted to an X-ray detector plate 131. The diverted coolant passes through the DL TEA 104, which is used to actively cool the detector 131. The volume of coolant that is diverted may depend on the respective cooling needs of the X-ray tube 129 and detector 131.

In an exemplary embodiment, the cooling need for the X-ray tube 129 may be in the kilowatt (kW) range with a magnitude of one or more kilowatts, while the cooling need for the detector 131 may be lower in the watt (W) range with a magnitude less than one kilowatt. In such an exemplary embodiment, a small portion of the coolant (e.g., coolant water, etc.) from the chiller 102 may thus be diverted to the DL TEA 104.

The remaining portion of the coolant is allowed to flow to the X-ray tube 129 for cooling purposes. Ultimately, the coolant is allowed to flow or return from the X-ray tube 129 and DL TEA 104 back to the active or passive chiller 102 for cooling.

Also shown in FIG. 3 are arrows 106, 108, 110, 112 representing the coolant flow or circulation via the pump 114 through the various conduits (e.g., tubes, hoses, tubing, pipes, etc.). Arrow 116 represents the coolant flow through the chiller 102. The arrow 106 represents the flow of coolant from the chiller 102 through hose 118 towards the X-ray tube 129 and X-ray image detector 131. The arrow 108 represents the flow of diverted coolant through the hose 120 to the DL TEA 104. The arrow 110 respresent the flow of coolant from the DL TEA 104 through the hose 122 heading back towards the chiller 102. The arrow 112 respresent the flow of coolant from the X-ray tube 129 through the hose 124 heading back towards the chiller 102.

The coolant flows 110 and 112 may be combined at location or juncture 126 before passing through the pump 114. For example, the coolant in hose 122 and the coolant in hose 124 may be combined via a valve, an installation configured to combine the coolant flow, etc. at the location or juncture 126.

The various hoses or other suitable fluid conduits used in this exemplary embodiment do not all need to be insulated. This is because the DL TEA 104 can regulate temperature within a wide range of coolant temperatures. It can also be beneficial to have heat leakage from the hoses to the environment.

When a passive chiller is used to cool the coolant, all of the hoses 118, 120, 122, and 124 are preferably not insulated as the inventor has found it is beneficial to have uninsulated hoses in the whole system when the passive chiller is used. But when an active chiller is used to cool the coolant, the hoses 120 and 122 may again preferably be hoses that are not insulated. But the other hoses 118 and 124 are preferably insulated.

When a passive chiller is used, the coolant may only be cooled down to a temperature that is above ambient temperature. As the coolant travels from the passive chiller 102 to the DL TEA 104 and X-ray-tube 129, the coolant loses heat and its temperature will drop. When an active chiller is used, the coolant will be below ambient temperature such that insulation is preferable to have on hoses 118 and 124 to avoid heat pickup as the coolant travels from the active chiller 102. By way of example, the detector plate temperature may be aimed at 30 degrees Celsius (° C.). In which case, uninsulated hoses 120 and 122 will have some heat pickup when an active chiller is used. This is preferable because it is assumed that the coolant has been cooled below 30° C. by the active cooler. With a passive cooler, the coolant would be close to 30° C. such that heat leakage or heat pickup will have a marginal effect. To summarize, hoses 120 and 122 may preferably be uninsulated regardless of whether the chiller is active or passive. Hoses 118 and 124 may preferably be uninsulated when a passive chiller is used, but insulated when an active chiller is used.

Also, the illustrated embodiment includes flexible corrosion resistant hoses without insulation and with a total length of about 20 meters. Alternative embodiments may include a different configuration for the conduits (e.g., longer, shorter, at least partially insulated hoses, polyvinyl chloride (PVC) tubing, corrugated plastic tubing, etc.).

Figure 4:
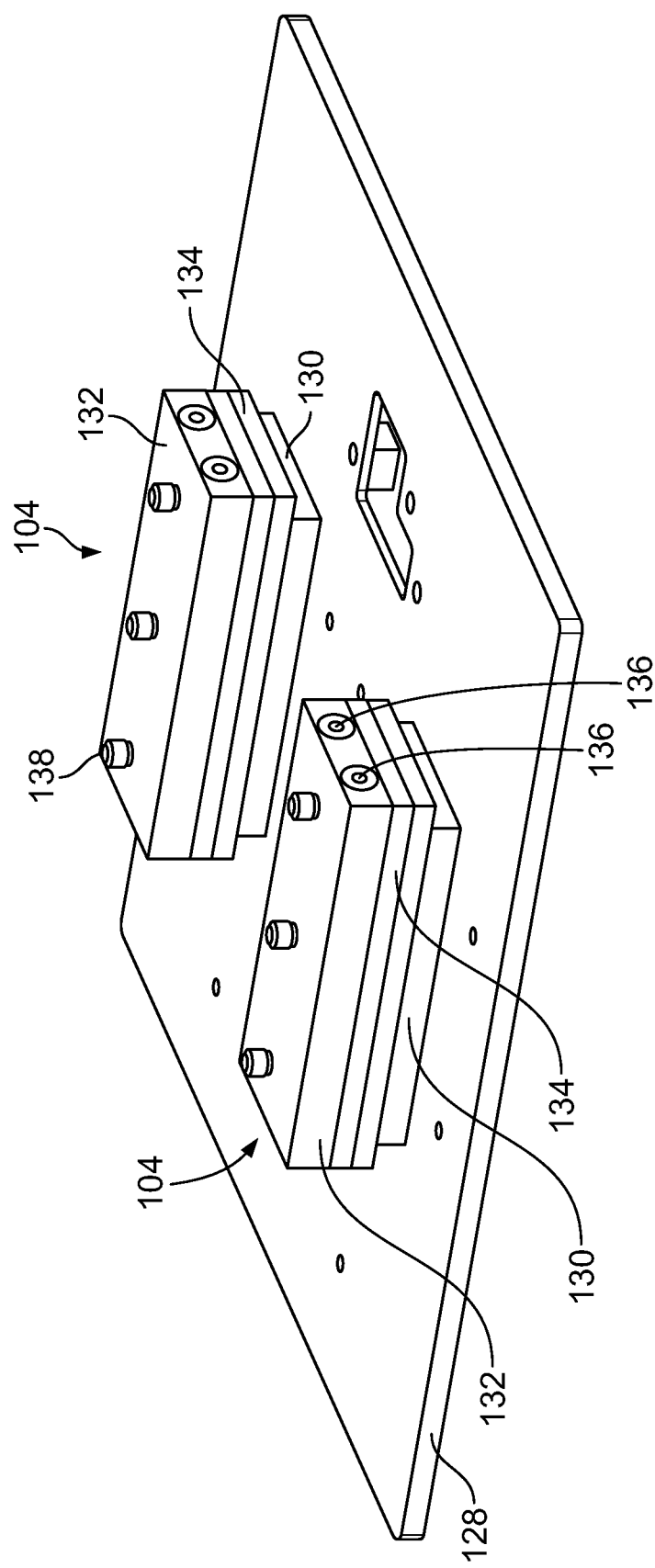
FIG. 4 illustrates a pair of direct-liquid (DL) thermoelectric assemblies (TEAs) positioned on a cold plate of an X-ray image detector according to an exemplary embodiment.

FIG. 4 shows a pair of direct to liquid or direct liquid (DL) thermoelectric assemblies (DL TEAs) 104 situated on a detector cold plate 128. Each DL TEA 104 includes an active direct plate heat exchanger or heat sink plate 130 on the bottom, which is situated on and/or in direct contact with the cold plate 128 of the detector. By way of example, the bottom part 130 may comprise a solid aluminum block as the active heat sink D-plate.

Each DL TEA 104 further includes a top part 132 that is the liquid block, which may also be referred to as a passive heat sink. Each DL TEA 104 further includes foam 134 in which is disposed a thermoelectric module (TEM). Because the TEMs are concealed within the foam 134, the TEMs are not shown in FIG. 4. Each thermoelectric module (TEM) is disposed generally between the top and bottom parts 132, 130 of the DL TEA 104.

With continued reference to FIG. 4, each DL TEA 104 includes an inlet/outlet 136 (e.g., openings, holes, connectors, etc.) on the side end thereof for the hoses. A hose will be coupled to the inlet to allow the DL TEA 104 to receive the coolant flowing from the chiller 102 through the hose. A hose will also be coupled to the outlet to allow coolant to be discharged from the DL TEA 104. Also shown in FIG. 4 are three screws 138 along the top of each TEA.

During manufacture of a TEA 104 shown in FIG. 4, through holes may be made (e.g., drilled, etc.) to create the inlet/outlet 136 and portions of the internal fluid flow channel within the TEA 104. To block the fluid from escaping or discharging out of the openings on the side of the TEA 104 opposite the inlet/outlet 136, screws (not show in FIG. 4) may be inserted into the through holes on the opposite side to block the coolant flow. Also a hole (not shown) may be formed (e.g., drilled, etc.) into the back side of the TEA 104 adjacent the opposite side. Then, a screw may be inserted into the hole to block the coolant flow. At which point, the TEA 104 will have a generally U-shaped fluid flow channel therein formed by the three holes made in the TEA 104 and screws used to block the flow. Accordingly, the coolant may flow in the inlet, through or around the U-shaped channel, and out the outlet, which is side-by-side or adjacent the inlet on the same side of the TEA 104 as the inlet.

With reference to FIGS. 3 and 4, the diverted coolant (e.g., water, etc.) may thus flow through hose 120 into the inlet in the passive side or top plate 132 of each DL TEA 104. By diverting or directing the coolant to the passive side 132 of the DL TEA 104 and having thermoelectric modules (TEMs) between the passive side 132 and direct plate heat exchanger 130, the temperature can be controlled directly on the cold plate 128 of the detector 131. Also, the detector cold plate 128 can both be cooled and heated by reversing polarity of the TEMs. Because the actual cooling or heating takes place directly on the cold plate 128, it is much easier to have a quicker regulation and also a more stable temperature than can be obtained with a distant chiller solution By way of example, the following advantages or benefits (but necesarily any or all) may be realized with the exemplary embodiment of a system 100 shown in FIG. 3. For example, the total cooling need may be reduced because the cooling takes place where it is needed instead of in a distant chiller. With a distant chiller, heat pickup in the hoses has to be accounted for, which, in turn, increases the cooling power needed. It is also more difficult to control temperature of a sensitive X-ray image detector when the chiller is distant or spaced far away. Advantageously, the exemplary embodiment of the system 100 shown in FIG. 3 provides cooling for an X-tray tube 129 and an X-ray image detector 131 using the single chiller 102. This provides a cost benefit because a second chiller is not needed as represented by the X through the second chiller at the bottom of FIG. 3.

Figure 5:
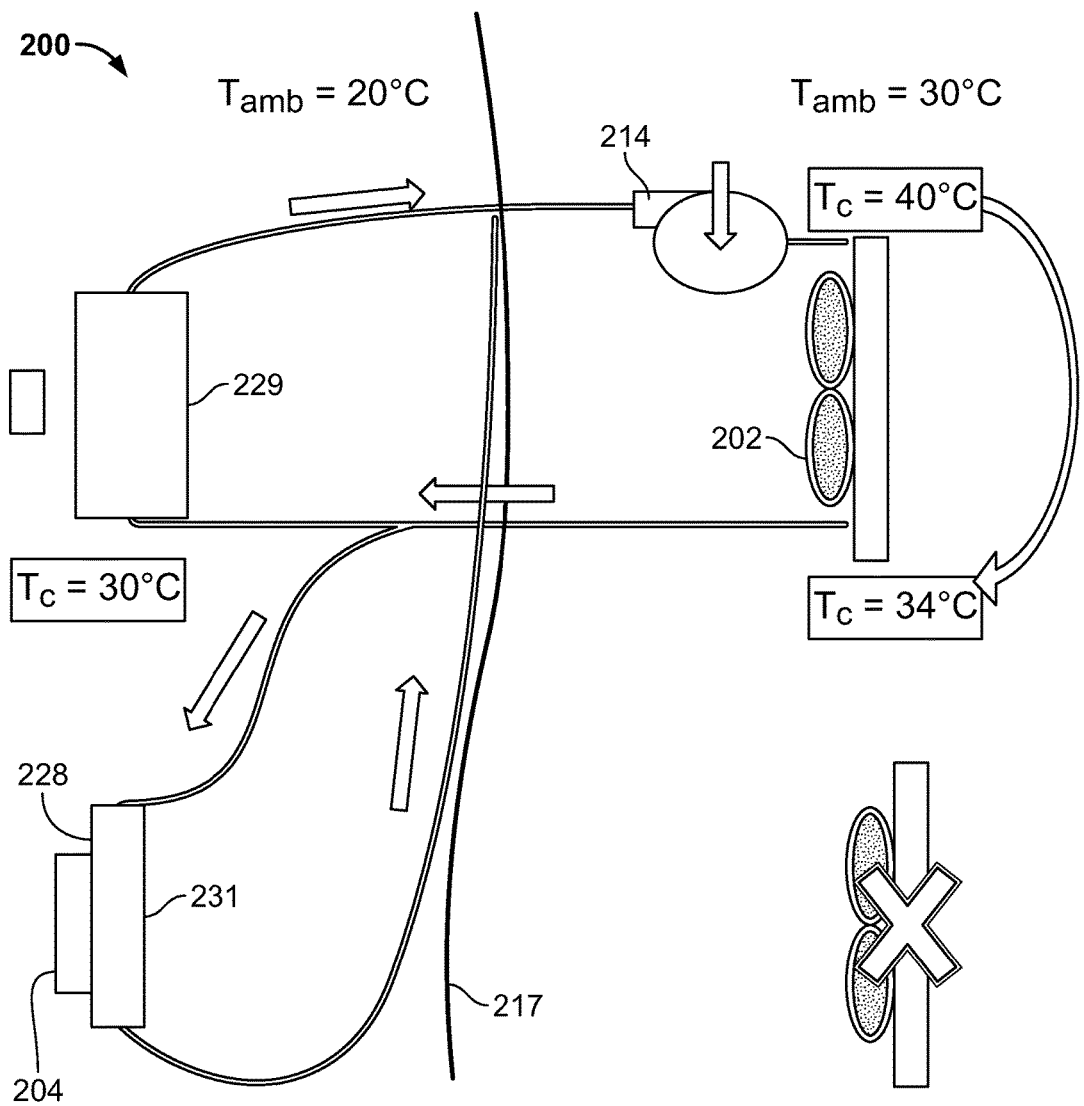
FIG. 5 illustrates another exemplary embodiment of a system for cooling an X-ray tube and an X-ray detector plate with a single chiller.

FIG. 5 illustrates another exemplary embodiment of system 200 embodying one or more aspects of the present disclosure. As shown, the system 200 may be used for cooling an X-tray tube 229 and an X-ray image detector 231 with a single chiller 202. Accordingly, the same chiller 202 from the X-ray tube 229 is also used for cooling the X-ray image detector 231. The chiller 202 may be situated in a technical room on an opposite side of a wall 217 than the X-ray tube 229 and X-ray image detector 231.

The chiller 202 may be an active or passive chiller depending on the cooling needs of the X-ray tube 229. By way of example only, the chiller 202 in this embodiment comprises a passive cooler, radiator, and fan which are used to cool a coolant (e.g., water glycol mix, etc.) outside the operating enviroment of the X-ray tube 229 and detector 231. The coolant is circulated via a pump 214 so that it flows through uninsulated conduits such that the temperature will drop even more through the long conduits.

Alternatively, the system 200 may include an active chiller having a built-in air conditioning (AC) loop that, along with a liquid to liquid heat exchanger, cools the secondary fluid comprised of water mixed with a corrosion inhibitant. The AC loop includes a compressor, a condensor, a fan, and an evaporator. The secondary loop with water consists of a heat exchanger, a pump, and an accumulator.

A portion of the coolant from the passive cooler 202 is diverted to an active DL TEA 204 situated on or mounted to an X-ray detector plate 228. The diverted coolant passes through the DL TEA 204 to actively cool the detector. The remaining features, components, operations, etc. of the system 200 may be similar to the corresponding features, components, operations, etc. of the system 100 described above.

In the example illustrated in FIG. 5, the system 200 includes two DL-120-24 cold plates from Laird Technologies, Inc., which provide more than enough cooling power. This illustrated embodiment also includes flexible corrosion resistant hoses without insulation and with a total length of about 20 meters. Alternative embodiments may include a different configuration for the conduits (e.g., longer, shorter, at least partially insulated hoses, polyvinyl chloride (PVC) tubing, corrugated plastic tubing, etc.). Likewise, the particular cold plate configuration and values set forth in FIG. 5 for $T_{amb}$ (ambient temperatures of 20° C. and 30° C.) and $T_c$ (coolant temperatures of 34° C. and 40° C.) are provided solely for purposes of illustration and not limitation. Other exemplary embodiments may be configured differently, such as with different cold plates and/or operable at different coolant temperatures. Accordingly, the exemplary length dimension, cold plate configuration, and temperature values are examples and not limitations.

Figure 6:
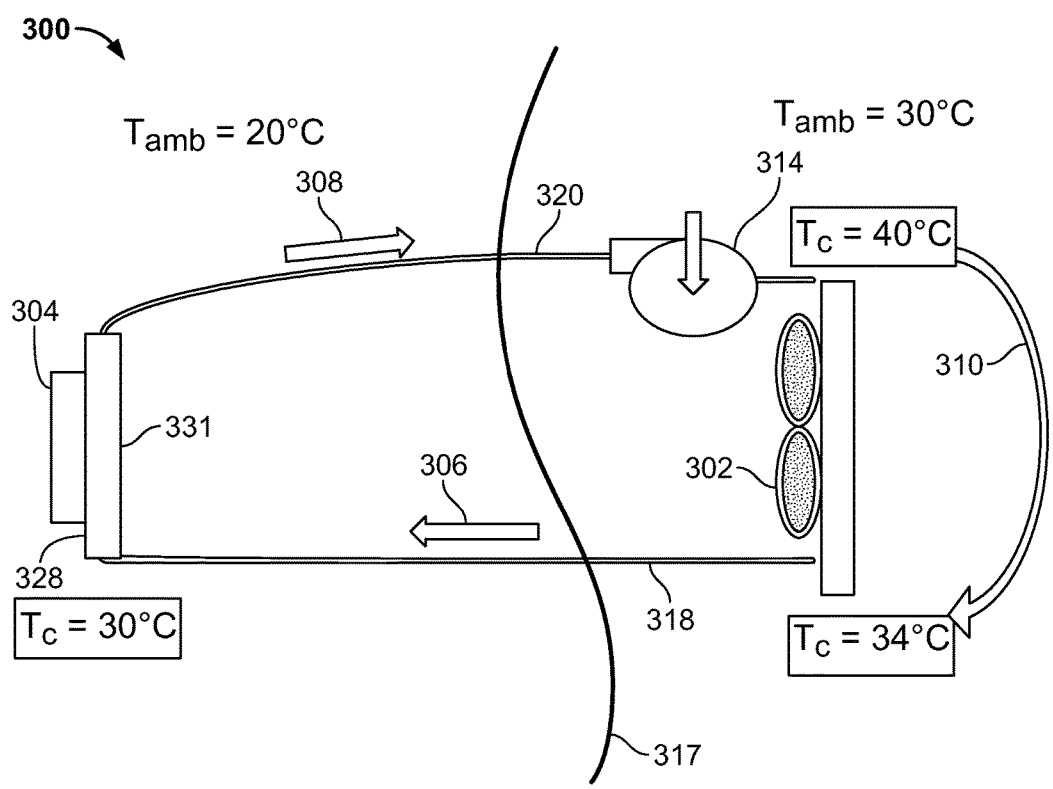
FIG. 6 illustrates another exemplary embodiment of a system for cooling an X-ray detector plate using direct-liquid (DL) thermoelectric assemblies.

FIG. 6 illustrates another exemplary embodiment of a system 300 embodying one or more aspects of the present disclosure. As shown, the system 300 may be used for cooling an X-ray detector plate 328 using one or more direct-liquid (DL) thermoelectric assemblies 304 situated on or mounted to the detector cold plate 328.

This exemplary system 300 includes a passive chiller 302. The chiller 302 comprises a passive cooler, radiator, and fan which are used to cool a coolant (e.g., water glycol mix, etc.) outside the operating enviroment of the X-ray tube and image detector 331. The chiller 302 may be situated in a technical room on an opposite side of a wall 317 than the X-ray image detector 331. The coolant is circulated via a pump 314 so that it flows through uninsulated conduits such that the temperature will drop even more through the long conduits.

Alternatively, the system 300 may include an active chiller having a built-in air conditioning (AC) loop that, along with a liquid to liquid heat exchanger, cools the secondary fluid comprised of water mixed with a corrosion inhibitant. The AC loop includes a compressor, a condensor, a fan, and an evaporator. The secondary loop with water consists of a heat exchanger, a pump, and an accumulator.

The coolant flows from the chiller 302 to an active DL (direct to liquid or direct liquid) thermoelectric assembly (TEA) 304. The DL TEA 304 is situated on or mounted to an X-ray image detector plate 328. The coolant passes through the DL TEA 304 to actively cool the X-ray detector 331.

Also shown in FIG. 6 are arrows 306 and 308 representing the coolant flow or circulation via the pump 314 through the various conduits (e.g., tubes, hoses, tubing, pipes, etc.). Arrow 310 represents the coolant flow through the chiller 302. The arrow 306 represents the flow of coolant from the chiller 302 through hose 318 towards the DL TEA 304. The arrow 308 represents the flow of coolant from the DL TEA 304 through the hose 320 heading back towards the chiller 302.

In the illustrated embodiment of FIG. 6, the system 300 includes two DL-120-24 cold plates from Laird Technologies, Inc. This illustrated embodiment also includes flexible corrosion resistant hoses without insulation and with a total length of about 20 meters. Alternative embodiments may include a different configuration for the conduits (e.g., longer, shorter, at least partially insulated hoses, polyvinyl chloride (PVC) tubing, corrugated plastic tubing, etc.). Likewise, the particular cold plate configuration and values given for $T_{amb}$ (ambient temperatures of 20° C. and 30° C.) and $T_c$ (coolant temperatures of 34° C. and 40° C.) are provided solely for purpose of illustration and not limitation. Other exemplary embodiments may be configured differently, such as with different cold plates and/or operable at different coolant temperatures. Accordingly, the exemplary length dimension, cold plate configuration, and temperature values are examples and not limitations.

By way of example, the following advantages or benefits (but necesarily any or all) may be realized with the exemplary embodiment shown in FIG. 6. Total cooling need may be reduced because the cooling takes place where it is needed instead of in a distant chiller. This is unlike systems that include a distant active chiller in which heat pickup in the hoses has to be accounted for, which, in turn, increases the cooling power needed. In this examplary embodiment, uninsulated hoses will help with dissipating heat, which will allow for reduced size of the passive cooler. This may allow for a more cost efficient system.

Accordingly, disclosed are exemplary embodiments of systems that may include direct-liquid thermoelectric cold plates and liquid heat exchangers, where a thermoelectric assembly is mounted directly to the object being cooled (e.g., X-ray detector plate, etc.) as opposed to being downline from the object being cooled. Advantageously, the disclosed exemplary embodiments may provide the advantage of better temperature control at the object to be cooled, reduced power consumption, elimination of the need for insulated tubes or hoses, elimination or removal of a second chiller, and/or reduced costs.

Also disclosed are exemplary methods of cooling X-ray tubes and X-ray image detector plates. In an exemplary embodiment, the method may include cooling a coolant (e.g., water glycol mix, etc.) outside the operating enviroment of the X-ray tube and X-ray image detector. This may include using an active or passive chiller. The method may also include diverting a portion of the coolant to an active DL TEA situated on or mounted to an X-ray detector plate such that the diverted coolant passes through the DL TEA to actively cool the detector.

The method may further include circulating, transferring, transporting, etc. the coolant through one or more uninsulated conduits, e.g., hoses, etc. such that the temperature of the coolant will drop even more through the long hoses. When a passive chiller is used to cool the coolant, uninsulated hoses may preferably be used to circulate the coolant from the passive chiller to the DL TEA and X-ray tube and back to the passive chiller. In this example, the inventor has found it is beneficial to have uninsulated hoses in the whole system when the passive chiller is used.

When an active chiller is used to cool the coolant, uninsulated hoses (e.g., hoses 120, 122 in FIG. 3, etc.) may again preferably be used to divert or circulate the coolant to/from the DL TEA. But insulated hoses (e.g., hoses 118, 124 in FIG. 3, etc.) may preferably be used to circulate the coolant from the active chiller and to return the coolant back to the active chiller.

As explained above, the coolant may only be cooled down to a temperature that is above ambient temperature when a passive chiller is used. As the coolant travels from the passive chiller to the DL TEA and X-ray-tube in exemplary embodiments, the coolant loses heat and its temperature will drop. When an active chiller is used, the coolant will be below ambient temperature such that it is preferable to have insulation to avoid heat pickup as the coolant travels from the active chiller. In one particular example, the detector plate temperature may be aimed at 30° C. In which case, uninsulated hoses (e.g., 120 and 122 (FIG. 3), etc.) will have some heat pickup when an active chiller is used. This is preferable because it is assumed that the coolant has been cooled below 30° C. by the active cooler. With a passive cooler, the coolant would be close to 30° C. such that heat leakage or heat pickup will have a marginal effect. To summarize, hoses 120 and 122 in FIG. 3 may preferably be uninsulated regardless of whether the chiller is active or passive. Hoses 118 and 124 may preferably be uninsulated when a passive chiller is used, but insulated when an active chiller is used.

By way of example only, any one or more of the exemplary embodiments disclosed herein may comprise one or more thermal management solutions from Laird Technologies, Inc. For example, a system disclosed herein may include a liquid cooling product (e.g., WLK Series, WL Series, OL Series, or liquid to liquid systems, etc.) from Laird Technologies, Inc. Information on various liquid cooling thermal management products from Laird Technologies, Inc. may be found at www.lairdtech.com.

In a particular exemplary embodiment, the chiller comprises a WLK60 recirculating chiller from Laird Technologies, Inc. that has a cooling capacity of 6000 watts. By using such a heavy duty chiller with a cooling capacity of 6000 watts for the X-ray tube, some of the cooling capacity (e.g., about 20 to 300 watts, etc.) can be spared and used for cooling the detector.

By way of background, a WLK Series recirculating chiller from Laird Technologies, Inc. is a compressor-based recirculating chiller that is operable for controlling the temperature of the coolant, e.g., water or water with glycol (antifreeze), etc. in a liquid circuit. The coolant is recirculated using a pump. Heat from the coolant is absorbed by a compressor-based system and dissipated to the ambient environment. The unit is regulated with a digital temperature controller with push button interface. The unit is housed inside a sheet metal casing. Depending on the particular cooling needs, other suitable chillers having a higher or lower cooling capacity may be used in other embodiments.

As a further example, a system disclosed herein may include one or more direct-liquid (DL) thermoelectric assemblies (e.g., DL-060-12-00, DL-120-24-00, DL-210-24-00, etc.) from Laird Technologies, Inc. Information on various thermoelectric assemblies from Laird Technologies, Inc. may be found at www.lairdtech.com.

In a particular exemplary embodiment, a pair of DL-120-24-00 thermoelectric assemblies are situated on and/or mounted to the cold plate of the detector. By way of background, the DL-120-24-00 thermoelectric assembly may be used to cool or heat either objects attached directly to the cold plate, or enclosures by attaching a thermal conductive container to the cold plate. Heat is dissipated to a liquid on the warm side of the DL-120-24-00 thermoelectric assembly. The liquid circuit is normally of a recirculating type with a pump and a liquid-to-air heat exchanger removing the heat into the ambient air. Other suitable thermoelectric assemblies may be used in other embodiments.

By comparison to exemplary embodiments disclosed herein, a previous solution uses chillers positioned very far away from the X-ray system to be cooled. The inventor hereof has recognized that this previous solution has to give extra cooling power as a countermeasure to offset or counter the losses in the long hoses to the object to be cooled. In exemplary embodiments disclosed herein, heat losses in the long hoses that are not insulated may be beneficial for the application leading to a more slim design using less power. This benefit may be realized as follows with the inventor's exemplary embodiments. For example, a passive chiller is unable to reduce the temperature of the coolant below ambient temperature. This means that the leakage or heat loss would be beneficial as the temperature of the coolant would decrease as the coolant travels through uninsulated hoses given that the coolant would lose or transfer heat to the outside environment via the hoses. As another example, an active chiller is able to reduce the temperature ($T_c$) of the coolant below ambient temperature ($T_{amb}$). This means that the coolant temperature ($T_c$) would increase as the coolant travels through uninsulated hoses due to heat transfer from the outside environment to the coolant via the hoses. But even if the coolant in this latter example were heated from, for example, 10° C. to 15° C., the coolant temperature would still be less than the temperature of the detector cold plate (e.g., typically about 30° C., etc.) Accordingly, the closer the coolant temperature ($T_c$) is to set point of the detector plate the less energy that is needed to cool or heat it.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. In addition, advantages and improvements that may be achieved with one or more exemplary embodiments of the present disclosure are provided for purpose of illustration only and do not limit the scope of the present disclosure, as exemplary embodiments disclosed herein may provide all or none of the above mentioned advantages and improvements and still fall within the scope of the present disclosure.

Specific dimensions, specific materials, and/or specific shapes disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter (i.e., the disclosure of a first value and a second value for a given parameter can be interpreted as disclosing that any value between the first and second values could also be employed for the given parameter). Similarly, it is envisioned that disclosure of two or more ranges of values for a parameter (whether such ranges are nested, overlapping or distinct) subsume all possible combination of ranges for the value that might be claimed using endpoints of the disclosed ranges.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The term "about" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. For example, the terms "generally", "about", and "substantially" may be used herein to mean within manufacturing tolerances. Or for example, the term "about" as used herein when modifying a quantity of an ingredient or reactant of the invention or employed refers to variation in the numerical quantity that can happen through typical measuring and handling procedures used, for example, when making concentrates or solutions in the real world through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements, intended or stated uses, or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method comprising:
   cooling a coolant outside an operating environment of an X-ray tube and an X-ray image detector using an active or passive chiller;
   circulating the coolant from the active or passive chiller towards the X-ray tube;
   diverting a portion of the coolant to a direct to liquid (DL)thermoelectric assembly (TEA) situated on an X-ray image detector plate such that the diverted portion of the coolant passes through the DL TEA, whereby the DL TEA is used for actively cooling and controlling temperature of the X-ray image detector plate;
   allowing at least a portion of the remaining undiverted coolant to flow to the X-ray tube for cooling of the X-ray tube; and
   returning the coolant from the X-ray tube and the DL TEA back to the active or passive chiller.

2. The method of claim 1, further comprising using the DL TEA to control temperature of the X-ray image detector plate directly on the X-ray image detector plate, whereby the X-ray image detector plate is both cooled and heated by the DL TEA by reversing polarity of one or more thermoelectric modules of the DL TEA.

3. The method of claim 1, wherein cooling the coolant includes using a single chiller such that the same single chiller is used for cooling both the X-ray tube and the X-ray image detector plate.

4. The method of claim 1, wherein the method includes:
   cooling the coolant includes using a passive chiller, and using uninsulated hoses to circulate the coolant from the passive chiller to the X-ray tube and the DL TEA and back to the passive chiller; or
   cooling the coolant includes using an active chiller, using insulated hoses to circulate the coolant from the active chiller to the X-ray tube and back to the active chiller, and using uninsulated hoses for the portion of the coolant diverted to the DL TEA.

5. A method comprising circulating a coolant from an active or passive chiller through a direct to liquid (DL) thermoelectric assembly (TEA) situated on an X-ray image detector plate such that the coolant passes through the DL TEA for actively cooling the X-ray image detector plate and for controlling temperature of the X-ray image detector plate, wherein:
   circulating a coolant from the active or passive chiller through the DL TEA comprises diverting a portion of the coolant from the active or passive chiller to the DL TEA such that the diverted portion of the coolant passes through the DL TEA; and
   the method further comprises circulating at least a portion of the remaining undiverted coolant from the active or passive chiller to flow to an X-ray tube for cooling of the X-ray tube.

6. The method of claim 5, further comprising using the DL TEA to control temperature of the X-ray image detector plate directly on the X-ray image detector plate, whereby the X-ray image detector plate is both cooled and heated by the DL TEA by reversing polarity of one or more thermoelectric modules of the DL TEA.

7. The method of claim 5, further comprising:
   cooling the coolant includes using a passive chiller, and using uninsulated hoses to circulate the coolant from the passive chiller to the X-ray tube and the DL TEA and back to the passive chiller; or
   cooling the coolant includes using an active chiller, using insulated hoses to circulate the at least a portion of the remaining undiverted coolant from the active chiller to the X-ray tube and back to the active chiller, and using uninsulated hoses to circulate the portion of the coolant diverted to the DL TEA.

8. The method of claim 5, further comprising:
   cooling the coolant outside an operating environment of the X-ray image detector plate using a single active or passive chiller; and
   returning the coolant from the DL TEA back to the single active or passive chiller.

9. The method of claim 5, wherein:
   the active or passive chiller comprises a compressor-based recirculating system operable for controlling a temperature of the coolant in a liquid circuit; and
   circulating a coolant from the active or passive chiller through the DL TEA comprise recirculating the coolant through the liquid circuit using a pump of the compressor-based recirculating system, such that heat is absorbed from the coolant and dissipated to the ambient environment.

10. A system comprising:
    an active or passive chiller for cooling a coolant;
    a direct to liquid (DL) thermoelectric assembly (TEA) situated on an X-ray image detector plate;

one or more conduits for circulating a coolant from the active or passive chiller to the DL TEA, whereby the coolant may pass through the DL TEA such that the DL TEA is usable for actively cooling and for controlling temperature of the X-ray image detector plate; and one or more conduits for returning the coolant from the DL TEA back to the active or passive chiller;

wherein the system is configured to divert a portion of the coolant from the active or passive chiller to the DL TEA and to circulate at least a portion of the remaining undiverted coolant from the active or passive chiller to an X-ray tube for cooling of the X-ray tube.

11. The system of claim 10, wherein the DL TEA comprises one or more thermoelectric modules that allow the X-ray image detector plate to be both cooled and heated by the DL TEA by reversing polarity of the one or more thermoelectric modules.

12. The system of claim 11, wherein the DL TEA is usable to control temperature of the X-ray image detector plate directly on the X-ray image detector plate.

13. The system of 10 wherein
the system includes only one said active or passive chiller such that the same said active or passive chiller is usable for cooling both the X-ray tube and the X-ray image detector plate.

14. The system of claim 10, wherein:
the active or passive chiller comprises a passive chiller and the one or more conduits comprise uninsulated hoses; or
the active or passive chiller comprises an active chiller, the one or more conduits comprise insulated hoses to circulate the at least a portion of the remaining undiverted coolant from the active chiller to the X-ray tube and back to the active chiller, and uninsulated hoses to circulate the portion of the coolant diverted to the DL TEA.

15. An X-ray system comprising an X-ray tube and an X-ray image detector plate cooled by the system of claim 10, wherein the active or passive chiller is located outside an operating environment of the X-ray tube and the X-ray image detector plate.

16. The X-ray system of claim 15, wherein the DL TEA comprises:
a bottom part situated on and /or in direct contact with the X-ray image detector plate; and
a top part having an inlet for receiving the coolant and a channel through which the coolant flows; and
one or more thermoelectric modules disposed generally between the top and bottom parts;
whereby temperature can be controlled directly on the X-ray image detector plate.

17. The X-ray system of claim 15, wherein the DL TEA comprises:
an active heat sink situated on and /or in direct contact with the X-ray image detector plate;
a passive heat sink having an inlet for receiving the coolant and a channel through which the coolant flows; and
one or more thermoelectric modules disposed generally between the active and passive heat sinks;
whereby temperature can be controlled directly on the X-ray image detector plate, which can be both cooled and heated by reversing polarity of the one or more thermoelectric modules.

18. The system of claim 10, wherein:
the active or passive chiller comprises a passive chiller; and the one or more conduits comprise first and second uninsulated conduits for circulating the diverted portion of the coolant respectively to and from the DL TEA, and third and fourth uninsulated conduits to circulate the at least a portion of the remaining undiverted coolant respectively to and from the X-ray tube; or the active or passive chiller comprises an active chiller; and the one or more conduits comprise first and second uninsulated conduits for circulating the diverted portion of the coolant respectively to and from the DL TEA, and third and fourth insulated conduits to circulate the at least a portion of the remaining undiverted coolant respectively to and from the X-ray tube.

19. The system of claim 10, wherein:
the system is configured to divert the portion of the coolant at a location upstream from the DL TEA and the X-ray tube such that only the diverted portion of the coolant passes through the DL TEA and such that only the at least a portion of the remaining undiverted coolant flows to the X-ray tube for cooling of the X-ray tube; and the system is further configured to combine the diverted portion of the coolant and the at least a portion of the remaining undiverted coolant at a location upstream of the active or passive chiller.

20. The method of claim 1, wherein the method includes:
diverting the portion of the coolant at a location upstream from the DL TEA and the X-ray tube such that only the diverted portion of the coolant passes through the DL TEA and such that only the at least a portion of the remaining undiverted coolant flows to the X-ray tube for cooling of the X-ray tube; and before returning the coolant from the X-ray tube and the DL TEA back to the active or passive chiller, combining the diverted portion of the coolant and the at least a portion of the remaining undiverted coolant at a location upstream of the active or passive chiller.

21. The method of claim 5, wherein the method includes:
diverting the portion of the coolant at a location upstream from the DL TEA and the X-ray tube such that only the diverted portion of the coolant passes through the DL TEA and such that only the at least a portion of the remaining undiverted coolant flows to the X-ray tube for cooling of the X-ray tube; and combining the diverted portion of the coolant and the at least a portion of the remaining undiverted coolant at a location upstream of the active or passive chiller.

* * * * *